United States Patent [19]

Stott

[11] Patent Number: 4,730,621

[45] Date of Patent: Mar. 15, 1988

[54] BLOOD PRESSURE MEASUREMENT

[75] Inventor: Frank D. Stott, Oxford, United Kingdom

[73] Assignee: National Research Development Corporation, London, England

[21] Appl. No.: 804,242

[22] Filed: Dec. 3, 1985

Related U.S. Application Data

[63] Continuation of Ser. No. 409,345, Aug. 18, 1982, abandoned.

[30] Foreign Application Priority Data

Aug. 21, 1981 [GB] United Kingdom ................. 8125592

[51] Int. Cl.$^4$ .............................................. A61B 5/02
[52] U.S. Cl. .................................... 128/667; 128/680
[58] Field of Search ................ 128/672, 677, 680–683, 128/686, 664–667

[56] References Cited

U.S. PATENT DOCUMENTS

| | | | |
|---|---|---|---|
| 3,051,165 | 8/1962 | Kompelien | 128/667 |
| 3,192,921 | 7/1965 | Erickson et al. | 128/667 |
| 3,229,685 | 1/1966 | Ringkamp et al. | |
| 3,412,729 | 11/1968 | Smith, Jr. | 128/667 X |
| 3,482,565 | 12/1969 | Gowen | 128/667 |
| 3,993,047 | 11/1976 | Peek | |
| 4,009,709 | 3/1977 | Link et al. | 128/683 X |
| 4,074,711 | 2/1978 | Link | |
| 4,105,021 | 8/1978 | Williams et al. | 128/683 |
| 4,117,835 | 10/1978 | Williams | |
| 4,271,843 | 6/1981 | Flynn | 128/681 |
| 4,406,289 | 9/1983 | Wesseling et al. | 128/672 X |

OTHER PUBLICATIONS

RCA Technical Notes, No. 1277, 28th Sep. 1981, Princeton, NJ, Marcus Nowogrodzki, "Detection of Arterial Pulse Shape".

European Search Report, Mar. 3, 1984.

Wood et al, "Measurement of Blood Content and Arterial Pressure in the Human Ear",—Staff Meetings of the Mayo Clinic, Jul. 5, 1950, pp. 398–405.

Brunner et al, "Comparison of Direct and Indirect Methods of Measuring Arterial Blood Pressure"-,—Medical Instrumentation, vol. 15, No. 1, Jan.-Feb. 1981; No. 2, Mar.-Apr. 1981; No. 3, May-Jun. 1981.

Primary Examiner—William E. Kamm
Assistant Examiner—Angela D. Sykes
Attorney, Agent, or Firm—Cushman, Darby & Cushman

[57] ABSTRACT

Blood pressure measurement apparatus comprises means for variably occluding a body zone by progressive application of external pressure between levels respectively above systolic and below diastolic, means for detecting variations in blood volume in said zone during variable occlusion thereof, and means responsive to the occluding and detecting means to indicate as systolic and diastolic pressures the values of said external pressure respectively when the maximum and minimum detected volume levels are each about half way between zero and the maximum level following the last minimum which does not depart significantly from zero. The blood volume variations are preferably determined by reference to light transmission through the zone, suitably infrared, but other measures are suitable as determined by strain gauge, proton magnetic resonance or microwave absorbtion.

4 Claims, 4 Drawing Figures

BLOOD PRESSURE MEASUREMENT

This is a continuation of application Ser. No. 409,345, filed Aug. 18, 1982, which was abandoned upon the filing hereof.

BACKGROUND OF THE INVENTION

The normal method of measuring blood pressure by non-invasive means entails the use of an inflatable cuff for location around the upper arm and some means for detecting the flow of blood at a location distal to the cuff. The cuff is inflated to a pressure at which the embraced tissue is compressed and all blood vessels therein, including the arteries, are occluded. The pressure in the cuff is then gradually reduced and the arteries start to open transiently to allow blood flow as soon as the cuff pressure falls below the peak systolic level. Thereafter, the arteries remain patent for an increasing proportion of the cardiac cycle as the cuff pressure is further reduced, until the pressure falls below the diastolic level. Following this last event, the arteries remain patent throughout the cycle and the flow of blood is determined only by the normal pressure cycle.

The distally located detecting means, which is commonly a stethoscope or an electronic equivalent, readily enables the first onset of blood flow to be detected at systolic pressure. However, at diastolic pressure the change in flow is much more subtle and difficult to detect because the flow approaches its unobstructed level at this time in an asymptotic manner. In the result, measurements of diastolic pressure are commonly inaccurate and of poor reproducibility.

In accordance with other proposals for measuring blood pressure, a cuff or equivalent device can be employed in association, at the same sit, with some means for detecting variations in the blood volume in the body zone embraced by the cuff as that zone is variably occluded. One such proposal (Wood et al, Staff Meetings of the Mayo Clinic, July 5, 1950, pages 398–405) suggests that systolic and diastolic pressure measurements are given by the cuff pressure when the detector respectively shows a first output and then a maximum output as the cuff pressure is continuously decreased from a level above systolic to one below diastolic. However, the results given with this proposal are such as to suggest no marked improvement over conventional methods of measuring blood pressure by non-invasive means. Again, the measurement of diastolic pressure is of poor accuracy.

An object of the present invention is to improve the above situation and this improvement rests on the finding that the blood volume in a body zone changes in two distinct phases when subjected to a progressive variation of externally applied pressure to or from a level causing occlusion of the zone, and that these two phases are respectively associated with transition of the external pressure through the systolic and diastolic levels.

BRIEF DESCRIPTION OF THE DRAWINGS

A fuller understanding of this finding, and of the invention and its operation will be gained by consideration of the accompanying drawings, in which.

DESCRIPTION OF THE PREFERRED EMBODIMENTS

Figure 1:
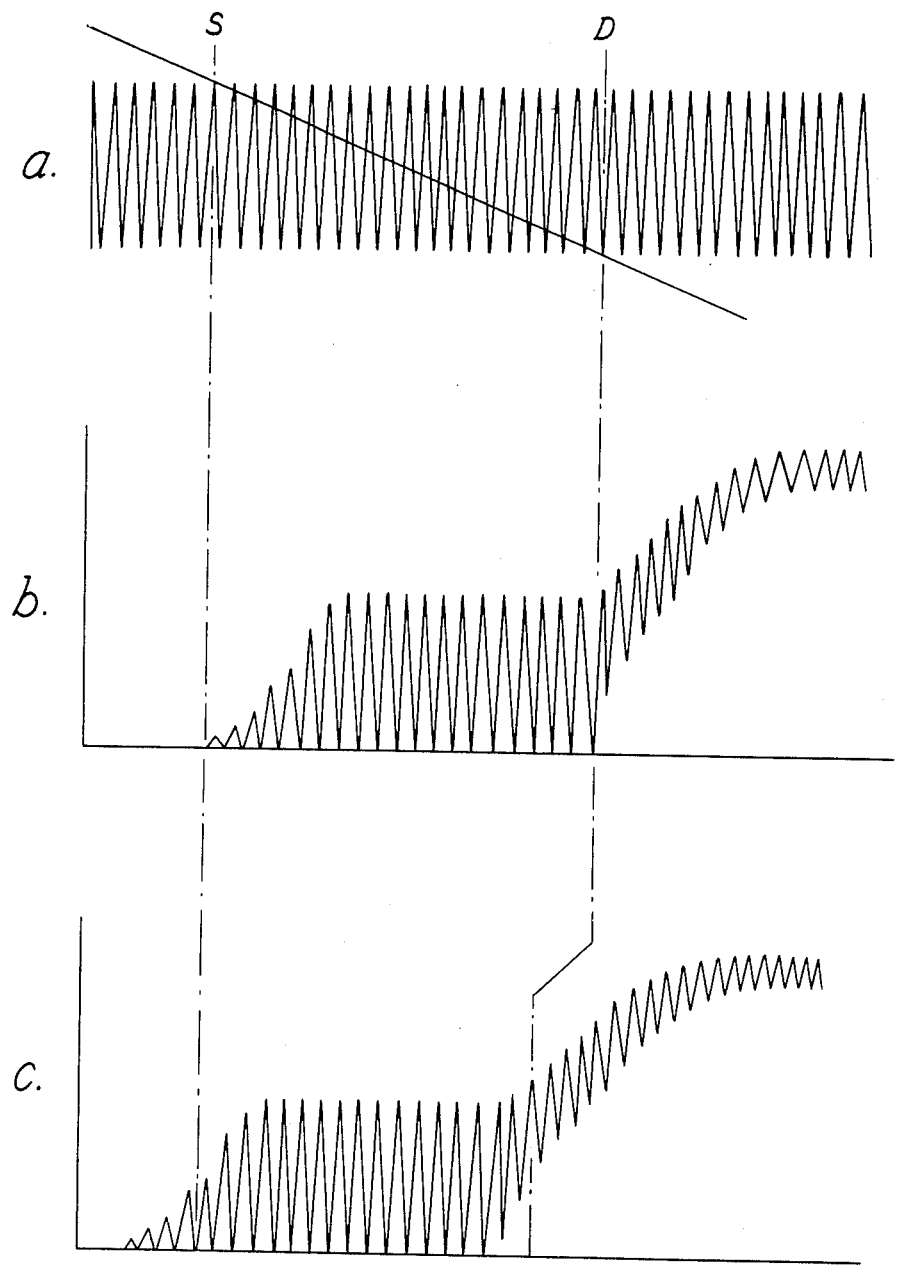
FIG. 1 graphically illustrates the operational basis for the invention.

FIG. 1 is in three parts of which the first, denoted (a), shows a cyclically repetitive waveform 1 having a triangular waveshape to represent in an idealised manner the pulsatile arterial blood pressure in a body zone to which the invention is to be applied. Across this waveform is superimposed a linearly declining characteristic 2 to represent external pressure applied to the body zone to occlude variably the same by uniform reduction from a pressure above systolic to one below diastolic.

The second part of FIG. 1, denoted (b), shows the resultant variation in blood volume which might be expected, from an idealised point of view, to be detected by the invention in the relevant zone. This detector output is noted at 3 and is seen to be of pulsatile form defining an envelope, shown in broken outline, of which the upper and lower boundaries 4 and 5 are respectively determined by the peaks and troughs of the individual pulses in the output 3.

Initially, when the external pressure is above systolic, all of the blood is squeezed out of the zone and there is accordingly no change in output from the detector.

As the external pressure falls to and below systolic, blood enters the arteries in the zone during that part of the pulse cycle during which the arterial pressure is higher than the former pressure, and is squeezed out again during the remainder of the cycle. This is indicated by the first occurrence of a detector output coincident with equality between the external and systolic pressures, which occurrence is denoted by a vertical chain line S through FIG. 1, the the upper boundary 4 of the detector output envelope thereafter progressively increasing during this first phase of blood volume variation, which phase is denoted at 6.

The continuing fall of the external pressure below systolic and towards diastolic can next produce a situation when the external pressure is lower than the arterial pressure throughout the cycle and at no time is all of the blood squeezed out of the arteries. Under these conditions the detector output is uniform, as is seen for the portion 7 in which the upper boundary 4 of the envelope is horizontal.

Finally, yet further decrease of the external pressure towards and beyond diastolic allows blood to enter and to remain in other parts of the vascular system in the zone; first the arterioles, then the capillaries, and lastly the venous system. During this second phase of blood volume variation the detector output increases again in conformity with the changes in the zone as denoted at 8. This is seen by a further elevation of the envelope upper boundary 4 and, because blood remains in some part of the vascular system in the zone throughout every pulse cycle, the lower boundary 5 is also seen to elevate from zero. The diastolic end point is clearly and unambiguously defined in this idealistic approach as the point at which these boundary elevations commence point is indicated by commencement of the further increase in and is denoted by the vertical chain line D through FIG. 1 when the external and diastolic pressures are equal.

In reality, development of the present invention shows a result as in the third part of FIG. 1, denoted (c), which is closely similar to that of FIG. 1(b) but is shifted in its relationship with FIG. 1(a).

The reason for this shift is that the vessels of the vascular system are not responsive to the various pressure changes in an ideal manner. More particularly, it is found that the vessels are not absolutely occluded by an external pressure equal to systolic, but rather a higher pressure is required. Correspondingly therefore, the first detector output occurs in FIG. 1(c) when the external pressure falls to this higher value, or some other value close thereto if there is any hysteresis in the action of the vessel.

A similar effect is found in connection with the transition from flow in the arteries to flow elsewhere in the vascular system, and the final phase of detector output variation occurs when the external pressure falls to a value in excess of diastolic.

These differences between idealised and real life situations are not found to be related in a precisely predictable manner because the general condition or so-called tone of the vascular vessels varies from one individual to another. Factors in such variation are age and disease.

However, it has been found that a close indication of the actual systolic pressure is obtained by attributing to it the value of the external pressure when the detector output upper boundary is half way between zero and the level of its uniformly horizontal portion. Similarly, it has been found that a close indication of the actual diastolic pressure is obtained by attributing to it the value of the external pressure when the detector output lower boundary reaches the same half way level just mentioned.

In practice, subject to the rate at which the external pressure is progressively varied and the tone of an individual vascular system, there may not be a readily discernible uniform portion in the detector output. Nevertheless, it is still readily possible to determine the relevant half way level because the uniform level is seen to be directly equatable with that of the last pulsatile peak in the detector output before the envelope lower boundary first elevates from zero.

The present invention provides apparatus for carrying out the procedure just described and accordingly comprises means for variably occluding a body zone by progressive application of external pressure between levels respectively above systolic and below diastolic, means for detecting variations in the blood volume in said zone during variable occlusion thereof, and means responsive to said occluding and detecting means to indicate the relevant values of said external pressure corresponding to the systolic and diastolic pressures.

This apparatus is open to variation in respect of the occluding and detecting means, but the former is at present preferably adapted for location around a relatively thin body zone, such as an ear lobe or finger, which allows detection on the basis of variation, with blood content, of light transmission through the zone.

Figure 2:
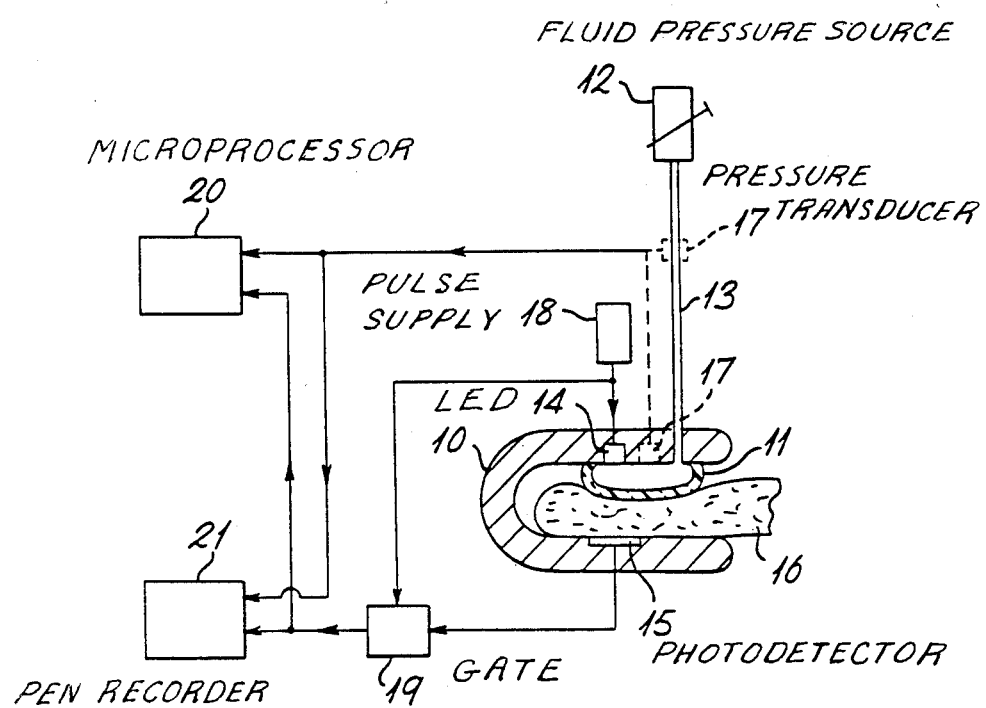
FIG. 2 diagrammatically illustrates one presently preferred form of the invention.

FIG. 2 diagrammatically illustrates one form of such preferred apparatus adapted for application about an ear lobe.

This apparatus comprises a pincer-like structure formed by a generally U-shaped rigid body 10 having an inflatable capsule 11 mounted on the inner face of the free end portion of one U-arm of the body 10. The capsule is made of an elastomeric material which is substantially uniformly light transmissive, and the capsule is inflatable by any suitably controllable source 12 of pressurised fluid communicated with the interior of the capsule by a tube 13 passing through the relevant arm portion of the body 10.

A light source 14, suitably of light emitting diode form, is mounted in the arm within the space defined by the capsule to face towards a photoelectric detector 15, suitably in the form of a silicon photovoltaic cell, mounted in the opposite arm of the body 10.

Use of this apparatus is largely self-evident from the foregoing discription. The body 10 is located about an ear lobe 16, and the capsule is first pressurised to occlude totally all blood vessels between the capsule and opposed arm, this being denoted by a constant output from the detector in response to light transmitted thereto by the source through the lobe. Thereafter the pressure in the capsule is reduced and an indication given of its values corresponding to systolic and diastolic pressures.

Clearly the apparatus will require a pressure transducer and various suitable forms are readily available. Generally speaking, two locations are preferred for such a transducer, the choice of location depending on the form of apparatus in question.

One such location is within the capsule or other pressure applying means, where the transducer will detect the pressure applied without error due to losses along the pressure fluid supply tube. This is relevant particularly when the pressure fluid is air or other gas. However, another factor is that the hydrostatic pressure variations in the vascular system relative to the heart as blood pressure source are preferably off-set by locating the transducer at the level of the heart. Location of the transducer within the capsule or other pressure applying means is accordingly best suited to apparatus applicable to a finger or other body zone readily movable to maintain this level.

The other location is apparent from these last comments, namely, within a separate unit connected by a flexible tube with the remainder of the apparatus, such unit being locatable over the heart. In this case, the pressure fluid is preferably water or other liquid so that pressure variations within the apparatus are minimised.

FIG. 2 shows in broken line a pressure transducer 17 in each of these alternative locations.

In operation of the apparatus the light source is preferably energised from a pulsed supply 18 to minimise power consumption, and the detector output is gated at 19 by the supply 18 so that response to external light sources, whether generally constant or flickering, is minimal.

The light source 14 suitably produces green light when applied to a body zone such as the ear lobe which is thin and without the presence of bone. The coefficient of absorption of green light in blood is high and transmission variations with blood content will be maximised in these circumstances. For other body zones, infrared light will normally be preferred because of its enhanced transmission through tissue.

Regarding the output indicator: this is suitably an appropriately designed microprocessor 20 responsive to the detector 16 and pressure transducer 17 to determine the relevant values by reference to the detector output variations as described above. The indicator output can involve digital display and/or printed record.

It will also often be desirable to have a printed record of the overall detector output and this can be provided by a pen recorder 21 or other suitable means.

Figure 3:
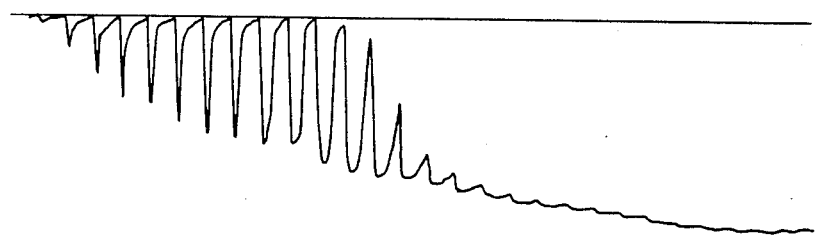
FIG. 3 graphically illustrates an output obtained with an embodiment of the invention.

While the invention has been described above as a specific illustrated embodiment, other comment has made it clear that the invention is open to variation. For example, blood volume detection by optical means is applicable in association with a conventional form of cuff for the finger or arm, the cuff preferably having the optical means moulded into is inner wall flush with the surface thereof. Indeed the latest development of the invention has involved a finger cuff form and FIG. 3 shows a typical pen recorder output obtained in such development, it being noted that blood volume level is shown by a downward excursion from the zero datum in this case.

Figure 4:
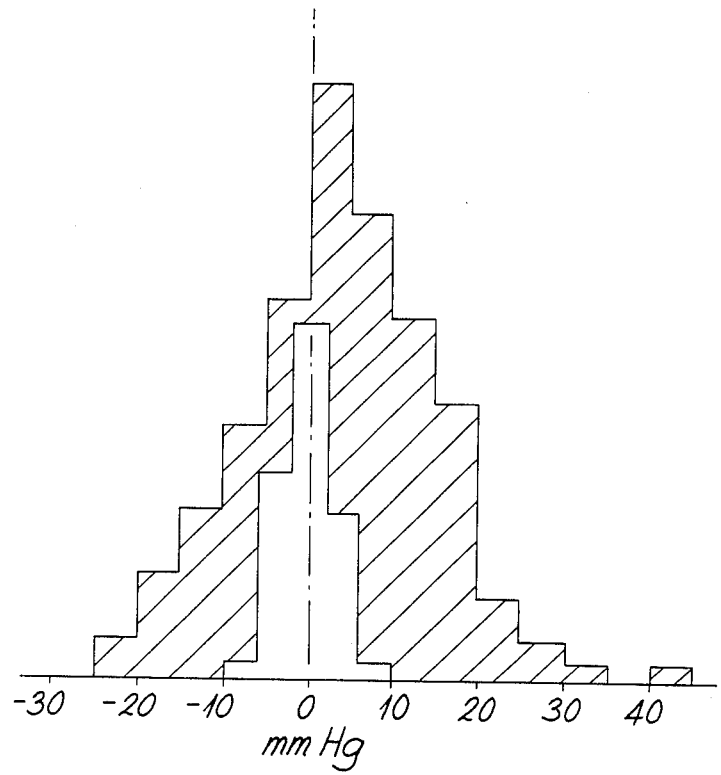
FIG. 4 is a histogram indicating the relative accuracy of a series of results obtained with the last-mentioned embodiment.

The overall improvement of the invention relative to the prior art is shown by the histogram of FIG. 4 in which the hatched area shows the errors obtained by conventional auscultation compared to intravascular measurement based on data from Bruneret et al (Medical Instrumentation 15; 1, 2 and 3; 1981) and the non-hatched area shows the clearly lesser errors obtained with a finger cuff according to the invention.

The possibility for variation also extends to the blood volume detecting means and alternatives to optical forms include a strain gauge to respond to variations of the body zone geometry with blood volume, proton magnetic resonance to respond to variation of fluid content, and microwave absorption, for example.

I claim:

1. A method of measuring blood pressure, comprising:
    variably occluding a body zone by progressive application of external pressure between values above that of systolic pressure and below that of diastolic pressure, such application being effected during a period extending over a plurality of successive cardiovascular pulses;
    detecting the maximum and the minimum levels of the blood volume in said zone for each of said pulses;
    identifying the one of said maximum levels next preceding the first one of said minimum levels to depart significantly from zero with reduction of said applied pressure;
    determining systolic pressure as the value of said external pressure when said maximum levels are about half way between zero and said one maximum level; and
    determining diastolic pressure as the value of said external pressure when said minimum levels are about half way between zero and said one maximum level.

2. A method according to claim 1 which comprises detecting said blood volume levels in response to variation, with blood content, of radiation transmission through said zone.

3. A method according to claim 2 wherein said radiation is light.

4. A method according to claim 2 wherein said radiation is infra-red.

* * * * *